United States Patent [19]

Crepin

[11] Patent Number: 5,070,009
[45] Date of Patent: Dec. 3, 1991

[54] PROCESS AND REAGENTS FOR THE DETECTION OF A MONOCATERNARY NUCLEIC ACID, PARTICULARLY A RNA IN A BIOLOGICAL MATERIAL AND PARTICULARLY IN LEUCOCYTE PREPARATIONS

[75] Inventor: Michel Crepin, Paris, France
[73] Assignee: Institut Pasteur, Paris, France
[21] Appl. No.: 246,004
[22] Filed: Sep. 15, 1988

Related U.S. Application Data

[63] Continuation of Ser. No. 657,236, Oct. 3, 1984, abandoned.

[30] Foreign Application Priority Data

Oct. 3, 1983 [FR] France .................................. 83 15726

[51] Int. Cl.$^5$ .............................................. C12Q 1/68
[52] U.S. Cl. ........................................ 435/6; 435/259;
435/270; 435/803; 435/810; 436/63; 436/64;
436/94; 436/501; 436/175; 436/813; 436/825;
935/4; 935/21; 935/75
[58] Field of Search ............... 435/516, 259, 270, 803,
435/810; 436/63, 64, 94, 501, 175, 813, 825;
935/4, 21, 78

[56] References Cited

U.S. PATENT DOCUMENTS 4,038,143 2/1977 Juni .
4,483,920 11/1984 Gillespie et al. ................ 435/179 X

FOREIGN PATENT DOCUMENTS 0070687 1/1983 European Pat. Off. .
83/02286 7/1983 PCT Int'l Appl. .
2019408 10/1979 United Kingdom .

OTHER PUBLICATIONS

Bresser, J. et al. *Proc. Nat'l Acad. Sci. U.S.A.*, vol. 80, 1983, pp. 6523–6527.
Perbal, B. *A Practical Guide to Molecular Cloning*, Wiley-Interscience, N.Y. 1984, pp. 388,389.
Bresser, J. et al, *DNA* vol. 2, No. 3, Sep., 1983, pp. 243–254.

*Primary Examiner*—Amelia Burgess Yarbrough
*Attorney, Agent, or Firm*—Burns, Doane, Swecker & Mathis

[57] ABSTRACT

The invention relates to a process for the in vitro detection of a determined RNA, particularly of a mRNA connected with a genetic abnormality in a biological material. This process comprises a treatment of the cells contained in that material for the sake of releasing their cellular components and of exposing the RNAs yet without denaturing other nucleic acids, and then the detection operation comprising contacting RNA sought to be detected, in presence of the other cellular components, with a nucleotidic sequence complementary of the RNA sought.

16 Claims, No Drawings

PROCESS AND REAGENTS FOR THE DETECTION OF A MONOCATERNARY NUCLEIC ACID, PARTICULARLY A RNA IN A BIOLOGICAL MATERIAL AND PARTICULARLY IN LEUCOCYTE PREPARATIONS

This application is a continuation of application Ser. No. 657,236, filed Oct. 3, 1984, now abandoned.

The invention relates to a process and to reagents for the detection of a nucleic acid which is normally monocatenary, such as a RNA, in a complex biological material, for instance in a tissue or, preferably, in a preparation of blood cells, such as leucocytes. It concerns more particularly the use of this process for detections in vitro of genetic abnormalities bringing into play defective genes, oncogens or exogenous genes capable of being incorporated into tissues, leucocytes or other cells of a host organism and to be expressed therein.

Under the expression "genetic abnormality" it should be understood either any genetic abnormality manifesting itself by its expression and implying consequently the early apparition of a messenger RNA (mRNA) which normally is not synthesized by the host, or to the contrary the absence or the disappearance of mRNA normally synthesized by the host. In the first case (apparition of a messenger RNA normally not present in the host) the mRNA may reflect either an alteration of the genetic patrimony of the host, or an induction of the expression of genes present in the organism yet normally unexpressed, or the invading or infiltration of the host's organism from whom the material was taken up by foreign constituents carrying genes likely of being themselves expressed in said host organism.

As examples of genetic abnormalities there may be mentioned oncogens which are often modified and which are expressed in corresponding tumors. A number of genes involved in oncogenesis have already been disclosed in the literature (Myb, Myc, Erb . . . ). For instance the Myc gene is activated in myelocytomatoses.

The expression products of pathogenic agents which had invaded the organism at an early stage may be among these products too.

It will be appreciated that the treatment of affections linked to such genetic abnormalities will be all the more efficient as they will have been detected earlier.

Accordingly the invention aims at providing a detection process which will reflect the earliest stages of the development of the affection to be detected. Therefore a particular interest has been given to the first sequences of the series of events which, at the biological level, culminate into expression products which are characteristic of the studied affection or abnormality. One of these first events consists in the transcription into mRNA of the genetic abnormality which provides it.

In a more general aspect, the invention also aims at providing a process enabling detections of the presence or not of a RNA in a biological medium, which process must both be more sensitive and easier to bring into practice than classical methods for the detection of a determined RNA. Particularly, the invention aims at overcoming the difficulties involved in the carrying out of classical processes, whereby the latter generally include extensive purifications of RNAs before the contact thereof with a probe likely to hybridize with the RNA sought can even be contemplated. More particularly an object of the invention is also to reduce in an important proportion the necessary preliminary treatments for obtaining a RNA preparation in a state appropriate for the carrying out of the detection steps, particularly by hybridization with a labelled probe. Consequently an object of the invention is also to reduce the losses of RNA to be detected as they are usual in conventional purification procedures.

In its broadest aspect, the process according to the invention for the detection of a determined genetic abnormality in a biological medium comprises effecting a treatment of the cells contained in said medium for causing the release of at least part of their internal cellular constituents, including messengers RNAs, and the exposure or unmasking of the latter RNAs in such manner as to make them accessible by hybridization to nucleotide sequences which are complementary therewith, this treatment being effected under sufficiently mild conditions so as to avoid any substantial denaturation of the bicatenary nucleic acids contained among the cellular constituents and contacting said RNAs with a probe containing a nucleotide sequence complementary of the RNA characteristic of the genetic abnormality, in the presence of said bicatenary DNAs and other cell constituents and components under conditions suitable for the hybridization of said probe with said characteristics RNA, and detecting the hybrid formed.

The invention applies with particular advantage to the detection of mRNAs involved in the expression of specific genes, as soon as suitable probes are available.

A first characteristic element of the invention comes from the discovery that the detection of a messenger RNA—or more generally of any RNA possibly present—in a biological medium becomes possible as soon as said RNA can be "exposed" or "unmasked", said exposure or unmasking involving an at least partial dissociation of the complexes which this RNA forms with other cellular constituents or components, particularly proteins. It is then no longer necessary to proceed with the complete purification of the RNA to be detected.

The second characteristic element of the process of the invention lies in the mild treatment as defined here above. The prevention of denaturation at least in substantial proportions of the bicatenary nucleic acids reinforces the selectivity of the subsequent hybridization operation of the specific RNA to be detected with the labelled probe. The bicatenary DNAs can then not interfere with the hybridization reaction.

The process of the invention for the detection of RNA is thus particularly advantageous because of its simplicity, its sensitivity, the latter being even further increased owing to the limitation to a minimum of the losses of the particular RNA to be detected.

The invention is also applicable to the detection of any monocatenary nucleotidic sequence foreign to the biological material under study. In that respect the invention may be applied to the detection of any various expression products, for instance, the expression products of the hepatitis B virus or of a retrovirus, the presence of which witnesses the development of a determined affection in the host from whom the biological sample was taken up. As an example of affection which can be diagnosed in vitro by the process of the invention one may mention lymphadenopathies or the acquired immune deficiency syndrome, by means of the detection of the retrovirus which appears to be connected therewith (F. BarréSinoussi, et al, Science, May 20, 1983, 220, 868.871).

A particularly important use of the invention takes place in the field of early in vitro diagnosis of malignant tumors or of leukemias. The invention provides results that are particularly significant as soon as an oncogenous gene (referred to hereafter under the expression "oncogen") linked to the type of tumor concerned has been identified. Under such circumstances the detection will be based on the performance of a hybridization between the corresponding mRNA whose production forms the first stage of the expression of the corresponding gene with a probe containing a nucleotidic sequence corresponding to said gene.

Experience has shown that the method of the invention can be used for the early detection of other tumors particularly primary solid tumors, even when oncogens specific to that type of tumor have not yet already been isolated. As a matter of fact it has been found that the development of a determined tumor within an organism is often accompanied by the induction of oncogens apparently not directly involved in the tumor concerned. This is what has been observed in the case of human mammary carcinomas which can be detected in vitro by the process of the invention, upon using a probe hybridizable with the Myc gene with a degree of certainty at least equal to that of the results provided by the other methods used in that field (if the anatomopathological slices are excepted).

A preferred biological material for carrying out that type of detection is formed of a blood cell preparation, preferably a preparation of leucocytes. The observations which have been made hereabove support consistently the hypothesis that the proliferation of tumoral cells in organisms is accompanied in most cases by an induction of large variety of the oncogens present to an extent sufficient to enable the detection of their expression by the process of the invention, by means of a probe complementary of one of them. Experience has further shown that the capability of an organism to be infiltered by lymphoblastoid cells originating from solid tumors exhibiting a highly inflammatory character is such that their detection is most efficiently carried out on the leucocytes obtained from a simple blood sample.

The invention is thus of particular significance in relation to accurate diagnosis and prognosis on the development of neoplasias which yield metastases (particularly pulmonary, ganglionic metastases . . . ), inasmuch as the degree of infiltration of the organism, particularly of the blood by the lymphoblastoid cells appears as being directly linked to the malignant character of the tumor.

The possibility of performing a diagnosis in vitro on a blood sample is of particular significance, especially if one bears in mind the character which can be uncertain of the biopsies that are often carried out today and used for the in vitro diagnosis. In addition to the real disagreement which biopsies present for patients who undergo them, it may be that they are not really taken up on the most significant area of the tumor, whereby the diagnositic may be mistaken. It goes nevertheless without saying that the invention can also be applied to a biological material consisting of a tumoral tissue, particularly as soon as a more refined in vitro diagnostic may be required.

The possibilities of use of the process according to the invention are not limited to the examples which have been indicated. It is applicable with particular advantage to the detection of any affection which involves the release in the circulating blood of expression products of particular genes, whether the affections have a cancerous character such as leukemias, or whether the affections are linked to chromosomal abnormalities or to viral infections.

In a preferred embodiment of the process according to the invention, the mild treatment of the cells to be treated comprises contacting the cells of the material under study, preferably blood leucocytes, with a non-ionic detergent, such as those known under commercial or non commercial designations, NONIDET 50 (NP 40), BR1J 35, desoxycholate, etc, then contacting the released cellular components which are likely to contain messenger RNAs with a solution of an ionic salt of high molarity, for instance a concentrated solution of potassium—or sodium—iodide in order to both dissolve and dissociate the complexes which the RNAs form with proteins or other components.

The cellular extracts may then be subjected to a procedure for the detection of a RNA complementary to that of the selected probe. Any known technique can be resorted to in that respect. It is advantageous to use the in situ hybridization technique on nitrocellulose. To that effect a small volume of the solution of the cellular extract and of the ionic salt is deposited on the cellulose filter. The latter is then washed with solutions which cause removal of the excess of the ionic salt and of the proteins. These washings are advantageously carried out with water, solutions of a ionic detergent such as sodium dodecylsulfate and ethanol. The latter also contributes to fixing the precipitated RNA on the filter and facilitates the later detection, when the filter is contacted with a labelled probe.

Any conventional technique may be used for labelling the probe. For instance the latter may be labelled radioactively or coupled (or is made couplable) to an enzyme which can be detected by the action which it may exert with respect to a determined substrate, or to a fluorescent molecule.

It is advantageous to carry out an acetylation or analogous of the filter, prior to performing the measurements underlying the detection, in order to avoid any background noises, such as those produced by the interaction between the nucleic acid probe with the charges of the filter.

The invention also relates to kits for the detection in vitro of a genetic abnormality under the conditions which have been defined hereabove. Such a kit, which is applicable particularly to a preparation of blood leucocytes, comprises a set of reagents among which:

one or several non ionic detergents which enable under appropriate conditions of dilution to dissolve the membranes of the cells contained in biological material to be treated;

ionic salts such as sodium—or potassium—iodides, to provide at the suitable concentration for the dissociation of the protein-RNA complexes contained in the treated material;

the components and buffers necessary for producing the solutions of said non ionic detergents and of said ionic salts at concentrations enabling the mild treatment of the cells of the aforementioned material, in order to cause the release of part at least of the internal cellular components, including messenger RNAs, and the exposure of the RNAs;

one or several labelled probes containing one nucleotidic sequence characteristic of the genetic abnormalities which is sought and means for performing the subsequent in situ hybridization of the RNA characteristic of the genetic abnormality sought with one or several of said labelled probes.

Advantageously, the kit comprises also means for carrying out an in situ hybridization between the one or several probes and the complementary RNA possibly present in the biological medium under study. The kit may then contain a filter or analogous device on which said RNAs may be deposited and a fixation reagent of the messenger RNA on the filter, such as ethanol, as well as reagents for the removal by washing of proteins, lipids and other residual cellular components.

This kit advantageously also comprises a reagent such as acetic anhydride dissolved in triethanolamine, that reagent being capable of preventing the fixation of the probe on the filter, through linkages other than those involved in the hybridization.

Advantageous solutions of the different reagents likely to be used efficiently in the carrying out of the process of the invention will preferably entail the following concentrations:

aqueous solution of the non ionic detergent: from 0.2% to 1% in volume of NP 40 or 0.2 to 1% in volume of desoxycholate, or mixture of the two solutions containing particularly from 20 to 80 parts of NP 40 and of from 80 to 20 parts of desoxycholate, preferably of 50 parts of the first and 50 parts of the second;

aqueous solution of sodium iodide or potassium iodide 5 to 13M;

solution of an ionic detergent, such as sodium dodecylsulfate: 0.2 to 2% in volume;

aqueous solution of ethanol: 50 to 100% ethanol per volume;

solution of acetic anhydride in triethanolamine: 0.05 to 0.2% mole of triethanolamine and from 0.1 to 0.5% in volume of acetic acid.

In the following, there will be disclosed by way of non limitative example an advantageous procedure for carrying out a typical assay of detection of the expression of an oncogene in a biological sample taken from a determined patient.

A blood sample is subjected to a treatment for lysing the red blood cells, for instance by contact with a solution of ammonium chloride. The sample is centrifuged at low speed, for instance at 1000 rpm for 5 minutes. The centrifugation sediment containing the leucocytes is recovered. The leucocytes are washed twice in a phosphate buffer (PBS) and dissociated in a mixture of 0.5% of the two detergents (NP 40 and desoxycholate). After incubation at 0° C. for a duration of from 5 to 15 minutes according to the nature of the tissue, the cells are treated at ambient temperature with a sodium iodide (NaI, 6.1M). The cellular extract obtained can be diluted into a NaI-saturated solution (12.2M) and a small volume (a few microliters) deposited on a nitrocellulose filter (Schleischer and Schüll). The filters are washed 5 minutes in water, then with a solution of 1% sodium dodecylsulfate. The filters are then washed three times for 5 minutes with a solution of 70% ethanol for removing the sodium iodide. Finally a washing for 10 minutes with 20 ml of a solution containing 0.25 ml of acetic anhydride in 100 ml of triethanolamine will provide for the removal of the background noise of the test. Filters are then dessicated and can be stored in a dessicator.

The filter is then treated and hybridized overnight with a labelled DNA probe (containing for example a sequence hybridizable with one of the oncogens Myc, Myb, Erb, etc.), for instance as disclosed by Wahl et al (1979). The hybridized homologue sequence (Myc, Myb, Erb) can for instance be detected by autoradiography of the radioactive probe or with an antibiotine-antiserum capable of recognizing the DNA probe, particularly when the latter is coupled (or can be coupled) to biotin. The intensity of the spot enables one to appreciate in an accurate manner the degree of expression of the oncogene per cell, per gram of tissue or per ml of blood. The filter containing an internal standard can then be rehybridized with another labelled probe.

The test has been used for the detection of human mammary carcinoma on biopsies or leucocyte samples taken from 25 human patients. 12 positive responses were noted. The results showed good correlation with those which had been achieved by the examination of anatomo-pathological slices.

To sum up it should be emphasized that the invention relates to a process and to reagents for the detection of any nucleic acid which by nature is normally monocatenary. This monocatenary nucleic acid will most often consist of a RNA, particularly a messenger RNA. It may also consist of a monocatenary nucleic acid normally foreign to the genetic patrimony of the cells of the biological material subjected to the detection. This monocatenary nucleic acid may consist of viral DNA or of a viral RNA.

The amount of DNA in such biological media exceeds considerably the amount of RNA sequences or other nucleic acids which by nature are normally monocatenary and which are present in said biological media at the same time. The concept underlying the invention was to provide a process which would permit the detection of such monocatenary nucleic acids, particularly RNAs, without having to first remove all other nucleic acids contained in the cells, i.e. to permit that detection without first having to subject the sample under study to considerable purification procedings.

Essentially the invention stems from the finding that RNAs can be unmasked or exposed in such manner as to be subsequently hybridizable with complementary nucleic acid sequences by mild treatments which are effective to dissociate the complexes which RNAs are likely to form with other cellular constituents or components without at the same time cause substantial denaturation of the bicatenary or double stranded DNAs. Thus the bicatenary nucleic acids present, i.e. most of the genetic patrimony of the cells concerned, will not interfere with the hybridization of the RNA (or monocatenary nucleic acid) sought with the complementary nucleic acid sequence of the probe subsequently brought into contact with the preparation.

The process has proven so selective and sensitive, that it enables the detection of the earliest stages of the development of an affection tied to the expression (or lack) of expression of any gene or nucleic acid likely to be expressed in the cell environment or the detection of oncogens induced by the early development of tumoral cells in the host's organism, even of oncogens not directly tied to the particular nature of the tumoral cells concerned.

I claim:

1. An in vitro diagnostic test for the detection of a genetic abnormality in cells in a liquid biological sample, the genetic abnormality being evidenced by the absence or presence of a single-stranded nucleotide sequence in said cells; said test consisting essentially of the steps of:

a) treating with a reagent consisting essentially of an ionic salt, complexes of RNAs and proteins from said cells; said ionic salt being present in an amount effective to dissociate said RNAs from said proteins, without simultaneously causing substantial denaturation of double-stranded DNAs present from said cells, and thereby to provide, in the presence of said double-stranded DNAs, unmasked RNAs that are hybridizable with nucleic acids containing complementary nucleotide sequences;

b) then depositing said unmasked RNAs on a filter suitable for in situ hybridization;

c) then washing said unmasked RNAs on said filter with an ionic detergent to remove proteins;

d) then treating said filter to remove background noise from said filter;

e) then contacting said unmasked RNAs on said filter with a DNA probe containing a nucleotide sequence complementary to said single-stranded nucleotide sequence evidencing said genetic abnormality under conditions allowing for the hybridization of said unmasked RNAs with said nucleotide sequence of said probe; and f) then determining, from the presence or absence of hybridization of the nucleotide sequence of said probe with said unmasked RNAs on said filter, the presence or absence in said cells of the single-stranded nucleotide sequence evidencing said genetic abnormality.

2. The test of claim 1 wherein said RNAs from said cells are messenger RNAs or viral RNAs.

3. The test of claim 1 wherein the nucleotide sequence of said probe is complementary to an oncogene.

4. The test of claim 1 wherein said biological sample is blood.

5. The test of claim 4 wherein said biological sample includes leukocytes.

6. The test of claim 1 which further comprises the step of contacting said biological sample with a dilute aqueous solution of a non-ionic detergent to release the contents of said cells, including said RNAs, from said cells before the treatment in step a) with said ionic salt.

7. The test of claim 6 wherein the concentration of the non-ionic detergent in the aqueous solution comprises about 0.2 to 1% by volume.

8. The test of claim 1 wherein the treatment in step a) with said ionic salt is carried out with a concentrated aqueous solution of an iodide salt.

9. The test of claim 8 wherein said concentrated solution consists essentially of water and said iodide salt.

10. The test of claim 8 wherein said concentrated solution of said iodide salt is a 5 to 13M solution of potassium iodide or sodium iodide.

11. The test of claim 10 wherein the treatment in step a) comprises a treatment with a 6.1M sodium iodide solution at ambient temperature followed by a treatment with a 12.2M sodium iodide solution.

12. The test of claim 1, wherein said ionic detergent is sodium dodecylsulfate.

13. The test of claim 12, wherein said filter is acetylated in said step d) to remove background noise from said filter.

14. The test of claim 13, wherein said filter is treated with acetic anhydride in said step d).

15. The test of claim 1, comprising a further step of washing said filter to remove said ionic salt between said steps c) and e).

16. The test of claim 15 wherein said filter is washed with ethanol in said further step.

* * * * *